(12) United States Patent
Roḡeau et al.

(10) Patent No.: US 8,157,864 B2
(45) Date of Patent: Apr. 17, 2012

(54) VERTEBRAL REPLACEMENT DEVICE

(75) Inventors: Dominique Roḡeau, Barcelona (ES); Mourad Bēn-Mokhtar, Geneva (CH)

(73) Assignee: Eden Spine Europe SA, Geneva (CH)

( * ) Notice: Subject to any disclaimer, the term of this patent is extended or adjusted under 35 U.S.C. 154(b) by 1319 days.

(21) Appl. No.: 11/808,025

(22) Filed: Jun. 6, 2007

(65) Prior Publication Data
US 2008/0004705 A1 Jan. 3, 2008

(30) Foreign Application Priority Data

Jun. 14, 2006 (EP) ...................................... 06012260

(51) Int. Cl.
*A61F 2/44* (2006.01)
(52) U.S. Cl. ................ 623/17.16; 623/17.15; 623/17.11
(58) Field of Classification Search ..... 623/17.11–17.16
See application file for complete search history.

(56) References Cited

U.S. PATENT DOCUMENTS

| 5,723,013 | A | 3/1998 | Jeanson et al. | |
|---|---|---|---|---|
| 6,176,882 | B1 * | 1/2001 | Biedermann et al. ...... | 623/17.15 |
| 2003/0045877 | A1 | 3/2003 | Yeh | |
| 2004/0049271 | A1 * | 3/2004 | Biedermann et al. ...... | 623/17.11 |
| 2005/0125061 | A1 * | 6/2005 | Zucherman et al. ....... | 623/17.11 |
| 2006/0200244 | A1 | 9/2006 | Assaker | |

FOREIGN PATENT DOCUMENTS

| EP | 0 188 954 A1 | 7/1986 |
|---|---|---|
| FR | 2 762 778 A1 | 11/1998 |
| FR | 2 850 563 A1 | 8/2004 |
| WO | WO 92/01428 A | 2/1992 |
| WO | WO 98/46173 A | 10/1998 |
| WO | WO 99/63913 A2 | 12/1999 |
| WO | WO 03/013399 A1 | 2/2003 |

OTHER PUBLICATIONS

Search Report of European Patent Office dated Apr. 10, 2007 Relating to European Application No. EP 06 01 2260.

* cited by examiner

*Primary Examiner* — Eduardo C Robert
*Assistant Examiner* — Julianna N Harvey
(74) *Attorney, Agent, or Firm* — Bacon & Thomas, PLLC

(57) ABSTRACT

A vertebral replacement device (1) includes a female part (2), a male part (3) that is mounted inside the female part (2) and can be axially displaced relative to the female part (2), first and second locking elements (14, 15) mounted so as to be movable in translation on the female part (2) in order to occupy a first position in which they cooperate with respective opposing parts (31) of a peripheral surface (6) of the male part (3) to axially lock the female and male parts (2, 3) relative to one another, and a second position in which the female and male (2, 3) parts can be freely displaced axially relative to one another, and a rotating control element (20) extending radially through the male part (3) this control element (20) cooperating with the locking elements (14, 15) so that, when a rotational movement is communicated to it, it transforms this rotational movement into a translational movement of each of the locking elements (14, 15) so as to bring the locking elements (14, 15) into either of the first and second positions.

13 Claims, 5 Drawing Sheets

VERTEBRAL REPLACEMENT DEVICE

BACKGROUND OF THE INVENTION

1. Field

The present invention concerns a device for replacing one or more vertebrae, designed to maintain a spacing between two vertebrae.

2. Related Art

There is a similar device, known from the document US 2006/0200244, comprising a male part mounted inside a female part, an anchor shoe guided in translation and fixed in rotation on the male part, an anchoring surface on the female part, and a control element that transforms a rotational movement into a translational movement of the anchor shoe so as to bring the shoe into a first position in which the male and female parts are fixed relative to one another or into a second position in which the female and male parts can freely slide axially relative to one another.

That device has the drawback that the male part is axially fixed relative to the female part on only one side, which in the long run can be prejudicial to the quality of the joint between the male and female parts and thus to the safe use of the device.

There is another vertebral replacement device, known from the document U.S. Pat. No. 5,723,013, comprising an elastic-walled male part and a female part. The male and female parts comprise complementary notches in the form of asymmetrical serrations. These asymmetrical notches allow a distraction displacement of the male and female parts via a sliding of the notches of the male part into the notches of the female part and an elastic deformation of the wall of the male part, and compression-lock the male and female parts.

The advantage of such a device is that it is easy to adjust the distance between the male and female parts, since it simply requires distracting the male and female parts until they reach the desired position, this distracting movement being irreversible. However, the elasticity given to the male part can, over time, weaken the device and thus adversely affect its safe use. Moreover, because the outer sleeve of the male part cooperates directly with the inner sleeve of the female part, the diameters of these sleeves must be very precise, which complicates production.

BRIEF SUMMARY OF THE INVENTION

The object of the present invention is to propose vertebral replacement devices which, in particular, are capable of offering exceptionally safe use.

DESCRIPTION OF THE DRAWINGS

Other features and advantages of the present invention will emerge through the reading of the following detailed description given in reference to the attached drawings, in which.

DETAILED DESCRIPTION OF PREFERRED EMBODIMENTS OF THE INVENTION

Figure 1:
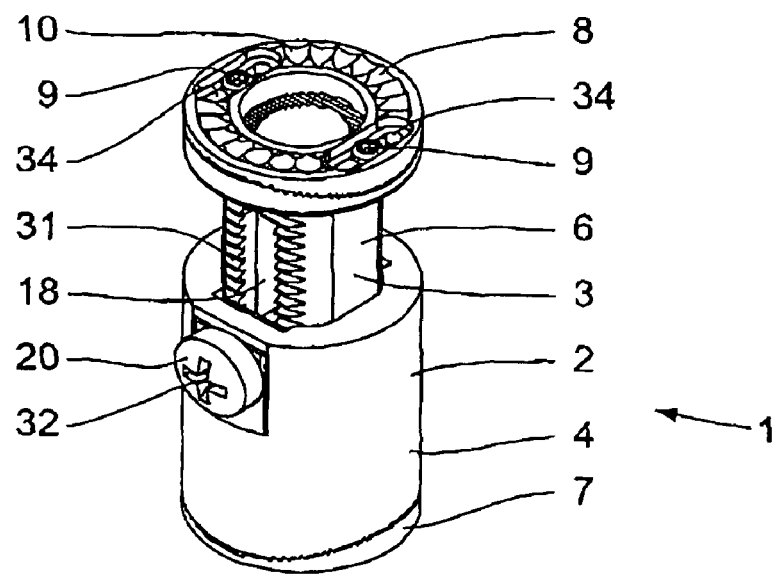
FIGS. 1 through 3 respectively show, in perspective and in two longitudinal sections taken in two perpendicular planes, a vertebral replacement device according to a first embodiment.
Figure 2:
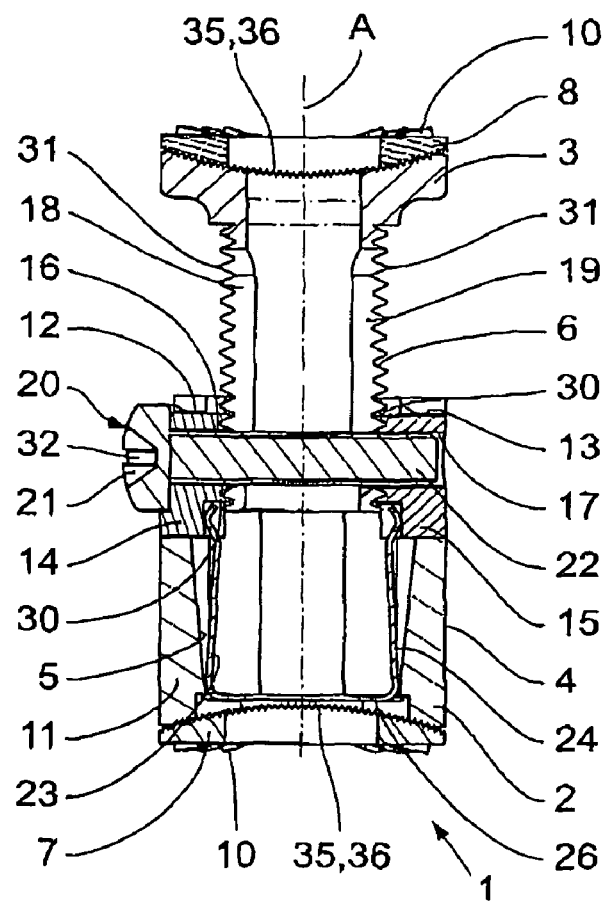
Figure 3:
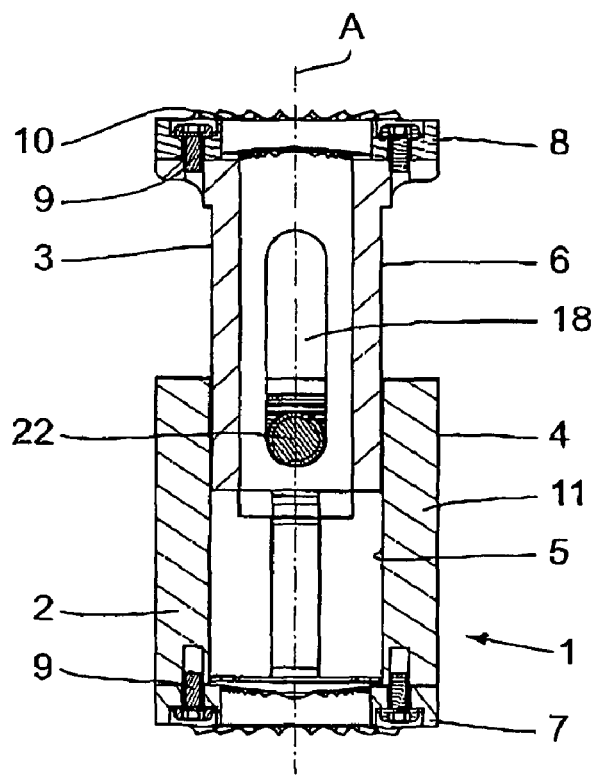

Referring to FIGS. 1 through 3, a vertebral replacement device or implant 1 according to a first embodiment of the invention comprises a female part 2 and a male part 3 partially inserted into the female part 2. The female and male parts 2, 3 are elongated hollow parts having a common longitudinal axis A. The outer peripheral surface 4 of the female part 2 has a circular cross-section. The inner peripheral surface 5 of the female part 2 and the outer peripheral surface 6 of the male part 3 have a round-cornered square or rectangular cross-section and are adapted to one another so as to allow the parts 2, 3 to slide axially relative to one another without, or with little, radial play. So-called lower 7 and upper 8 plates are respectively attached to the female and male parts 2, 3 by screws 9 and comprise anchoring elements 10 for anchoring the device 1 into the supra- and subjacent vertebrae.

The female part 2 comprises in its peripheral wall 11 two diametrically opposed housings 12, 13 in which two anchor shoes 14, 15 are guided in radial translation, i.e., in a direction orthogonal to the axis A. The housings 12, 13 and the shoes 14, 15 have complementary square or rectangular shapes, thus preventing the shoes 14, 15 from rotating inside the housings 12, 13. The shoes 14, 15 each comprise a through-bore 16, 17 located opposite a respective oblong hole 18, 19 provided in the peripheral wall of the male part 3. The bores 16, 17 and the holes 18, 19 allow a control screw 20 to pass through the shoes 14, 15 and the male part 3.

The screw 20 comprises a head 21 and a shaft 22. The end of the shaft 22 farthest from the head 21 is threaded and cooperates with a tapping in the bore 17 of the shoe 15. The other end of the shaft 22, near the head 21, does not include a threading. The shoe 14 is freely mounted around this other end.

Figure 4:
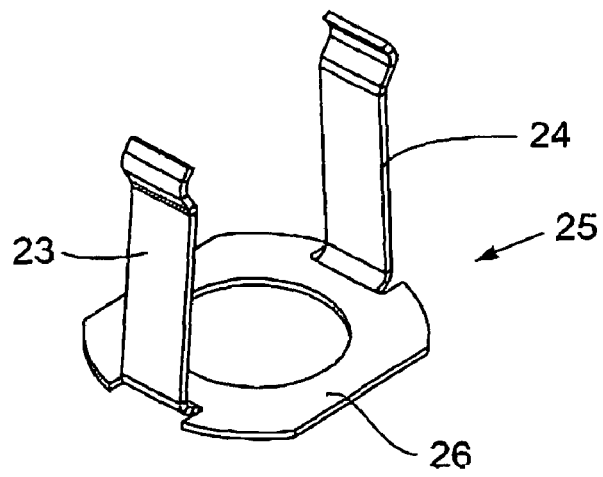
FIG. 4 shows, in perspective, a part defining spring leaves used in the device according to the first embodiment of the invention.

The shoes 14, 15 are subjected to an elastic action which tends to separate them from the male part 3. This elastic action is exerted by two identical spring leaves 23, 24, respectively acting on the shoes 14, 15. The spring leaves 23, 24 are part of the same unitary part 25, shown in FIG. 4, which part includes a rigid base 26, which rests on the bottom of the female part 2 and from which the leaves 23, 24 extend substantially parallel to the axis A.

Figure 5:
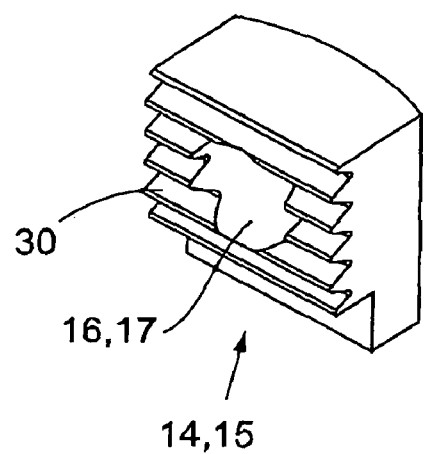
FIG. 5 shows, in perspective, a shoe used in the device according to the first embodiment of the invention.
Figure 6:
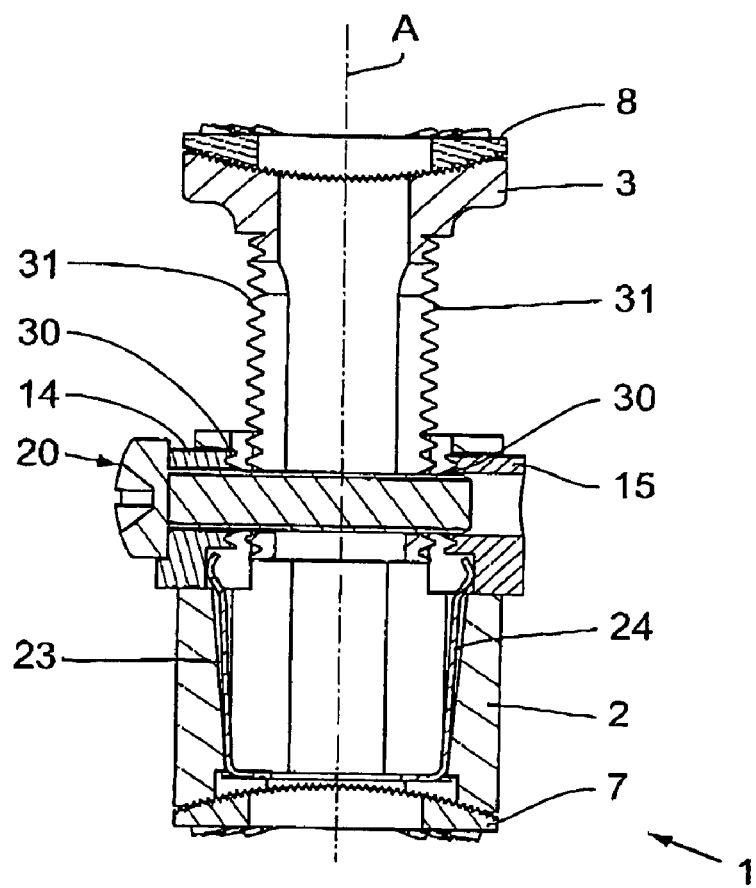
FIG. 6 shows, in longitudinal section, the vertebral replacement device according to the first embodiment of the invention, in a state in which the male and female parts of this device can slide freely relative to one another.

As shown in FIGS. 1, 2 and 5, the surfaces of the shoes 14, 15 and of the male part 3 that face each other include complementary serrated notches 30, 31. These notches 30, 31 cooperate with one another when the shoes 14, 15 are in a first position (FIG. 1, 2), anchored in the outer peripheral surface 6 of the male part 3, and no longer cooperate with one another when the shoes 14, 15 are in a second position, apart from the male part 3 (FIG. 6). In their first position, the shoes 14, 15 completely immobilize the female and male parts 2, 3 relative to one another. In the second position of the shoes 14, 15, the female and male parts 2, 3 are free to slide relative to one another along the axis A, thus allowing the surgeon to adjust the spacing between the plates 7, 8, within limits defined by the oblong holes 18, 19 against whose wall the shaft 22 of the screw 20 can come to a stop. A rotation of the female and male parts 2, 3 relative to one another about the axis A is prevented or limited by the oblong holes 18, 19, which have a width equal to or slightly larger than the diameter of the shaft 22.

The translation of the shoes 14, 15 from either their first or second position to the other is driven by a rotation of the control screw 20 about its axis, which rotation can be communicated by means of a screwdriver received in a corresponding recess 32 of the head 21. Rotating the control screw 20 in one direction moves the shoes 14, 15 closer to the male part 3, thus bringing them into the first position, while rotating the control screw 20 in the other direction moves the shoes 14, 15 away from the male part 3, thus bringing them into the second position. More precisely, when the screw 20 is turned in the first direction, the shoe 14 is pushed by the head 21 until it comes to a stop against the male part 3 while the other shoe 15, driven by the screw 20 like a rotationally fixed nut, moves closer to the male part 3 until it comes to a stop against it, these movements of the shoes 14, 15 taking place in opposition to the elastic action exerted by the spring leaves 23, 24. When the screw 20 is turned in the second direction, the shoes 14, 15 are moved away from the male part 3 under the action of the springs 23, 24.

It is clear that the locking of the female and male parts 2, 3 into position, obtained when the screw 20 is fully tightened, is particularly reliable since it occurs at two diametrically opposed points of the male part 3. This locking, moreover, is easily performed, by rotating a single control screw 20 that can be accessed from one side of the device.

In a variant of embodiment (not represented), the end of the shaft 22 of the screw 20 near the head 21 includes a threading whose pitch is reversed relative to that of the other end of the shaft 22. This threading cooperates with a corresponding tapping of the shoe 14.

Figure 7:
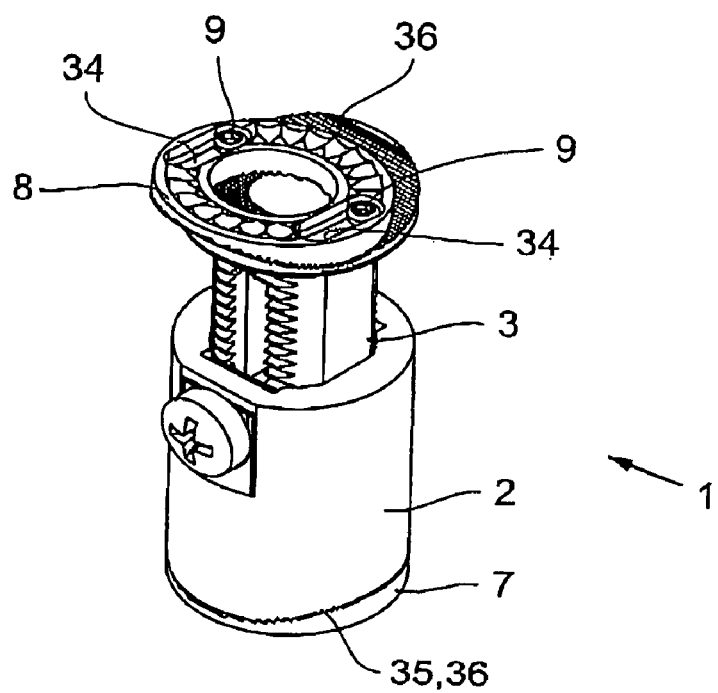
FIGS. 7 and 8 respectively show, in perspective and in longitudinal section, the device according to the first embodiment of the invention with an upper plate in an adjusted inclined position.
Figure 8:
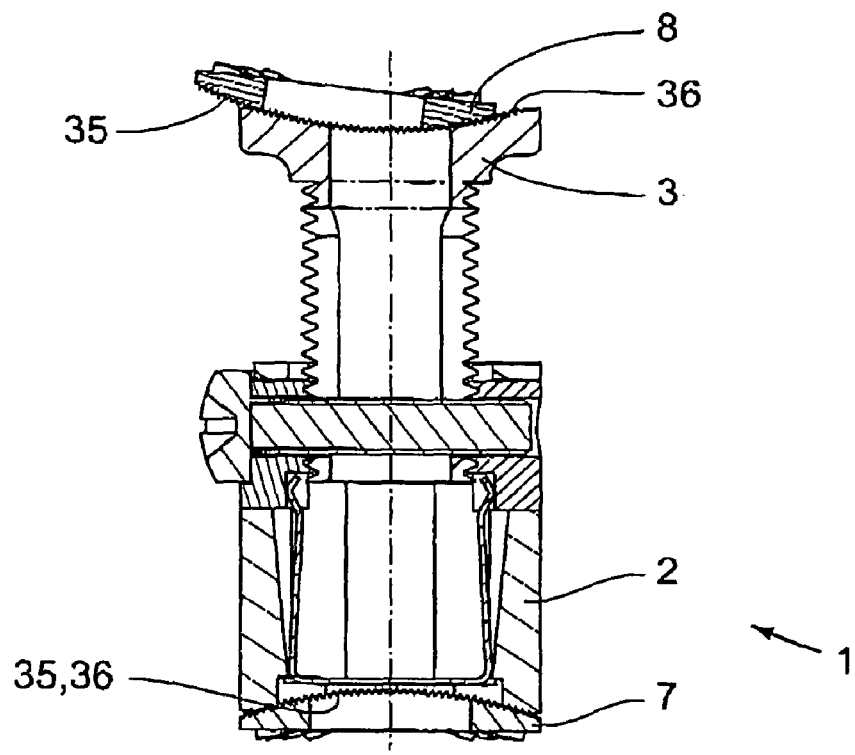

According to another feature of the invention, the inclination of the plates 7, 8 relative to the axis A of the female and male parts 2, 3 is adjustable. As may be seen in FIGS. 1 and 7, the screws 9 used to fasten the plates 7, 8 to the lower surface of the female part 2 and the upper surface of the male part 3, respectively, cooperate with oblong through-holes 34 of the plates 7, 8. Moreover, the upper surface of the lower plate 7 and the lower surface of the female part 2 have complementary notches 35, 36 and an arc-shaped profile, respectively convex and concave, with the same center and the same radius. These surfaces are held against one another by the screws 9, while the notches 35, 36 cooperate with one another to define and maintain the inclination of the plate 7. The lower surface of the upper plate 8 and the upper surface of the male part 3 also have complementary notches 35, 36 and an arc-shaped profile, respectively convex and concave, with the same center and the same radius. These surfaces are held against one another by the screws 9, while the notches 35, 36 cooperate with one another to define and maintain the inclination of the plate 8, as shown in FIGS. 7 and 8. The notches 35, 36 have a serrated profile and extend in a direction orthogonal to that in which the oblong holes 34 are oriented. To adjust the inclination of the plates 7, 8 (cf. FIGS. 7, 8), the surgeon partially unscrews the plates 7, 8 to separate the notches 35, 36, displaces the plates 7, 8 relative to the female and male parts 2, 3 in the direction of the oblong holes 34 and positions them appropriately by means of the notches 35, 36, then re-screws the plates 7, 8.

Figure 9:
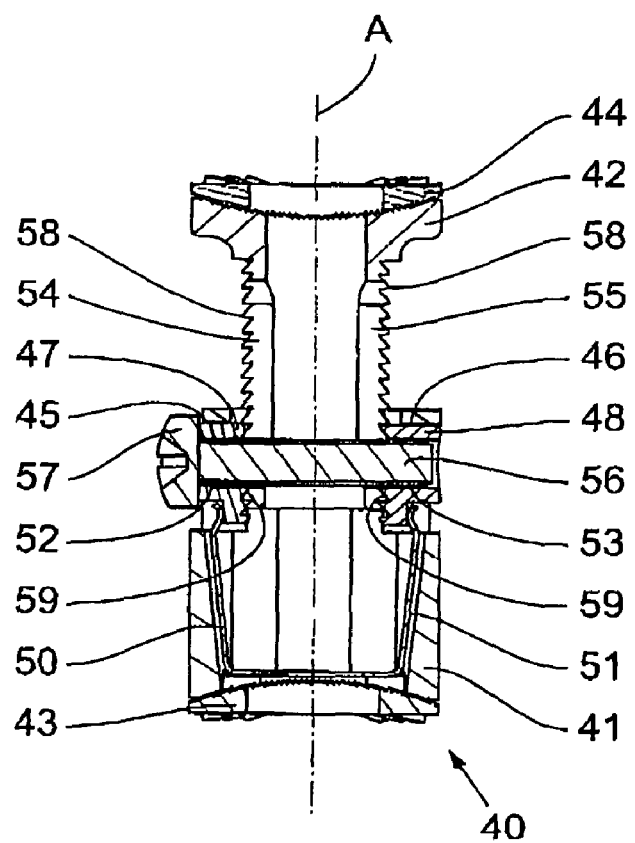
FIG. 9 shows, in longitudinal section, a vertebral replacement device according to a second embodiment.
Figure 10:
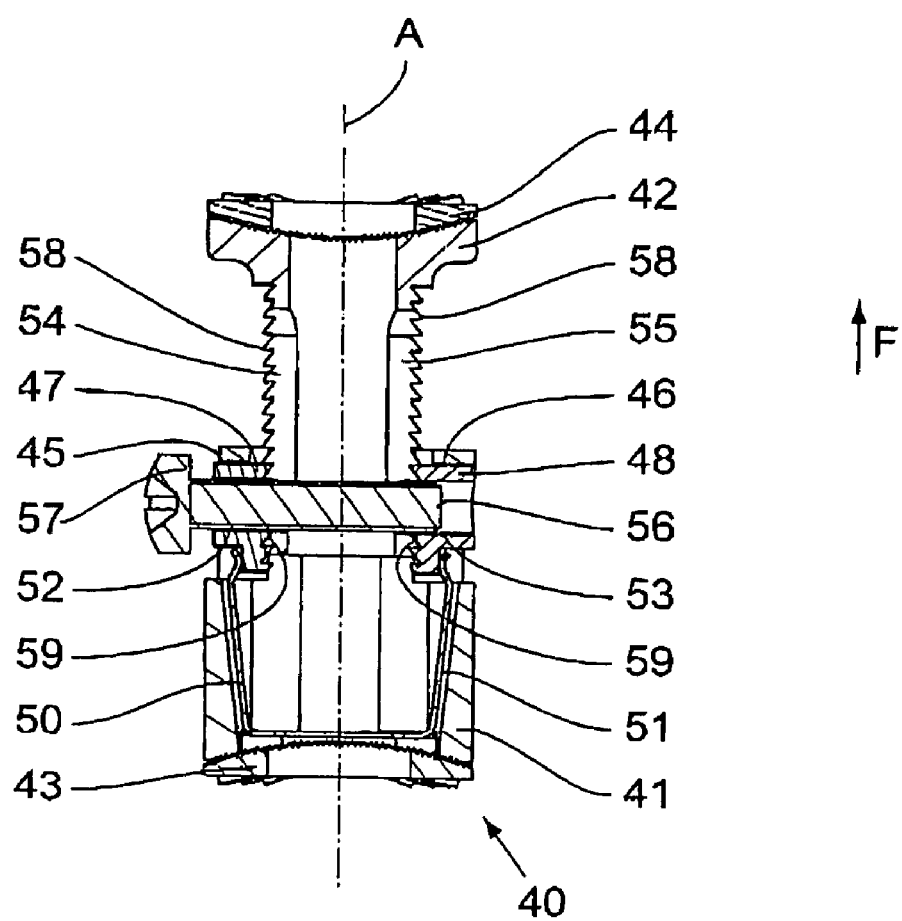
FIG. 10 shows, in longitudinal section, the vertebral replacement device according to the second embodiment in a state in which a locking screw is loosened so as to allow the spacing between the male and female parts of this device to be adjusted.

FIG. 9 shows a vertebral replacement device 40 according to a second embodiment of the invention. The device 40 comprises female and male parts 41, 42 of the same shape as the parts 2, 3 of the device 1 according to the first embodiment and to which are fastened lower and upper adjustably inclinable plates 43, 44, identical to the plates 7, 8. As in the first embodiment, the peripheral wall of the female part 41 comprises two diametrically opposed housings 45, 46 which receive notched shoes 47, 48 that are guided in radial translation but rotationally fixed inside the housings 45, 46. The shoes 47, 48 are subjected to the action of two spring leaves 50, 51 which are part of the same unitary part placed on the bottom of the female part 41. Through-bores 52, 53 provided in the shoes 47-48 and oblong holes 54, 55 provided in the peripheral wall of the male part 42 and identical to the holes 18, 19 of the device 1 allow the passage of the shaft 56 of a screw, the end of which shaft 56 furthest from the screw head 57 is threaded and cooperates with a tapping of the bore 53 of the shoe 48, while the end nearest the head 57, around which the shoe 47 is placed, is unthreaded, thus allowing the screw 56, 57 to rotate freely relative to the shoe 47. This device 40 differs from the device 1 according to the first embodiment in that:

the spring leaves 50, 51 exert an elastic action on the shoes 47, 48 that keeps them in continuous contact with the serrated notches 58 of the male part 42, the screw 56, 57 performs a simple locking function, and not a function for controlling the position of the shoes 47, 48, the notches 58 of the male part 42 and the complementary notches, 59 of the shoes 47, 48 are asymmetrical so as to allow, when the screw 56, 57 is sufficiently loosened (FIG. 10), a distraction sliding of the male part 42 relative to the female part 41, i.e. in the direction of the arrow F in FIG. 10, by sliding the notches 58 of the male part 42 into those 59 of the shoes 48, 48 in opposition to the action of the spring leaves 50, 51, and so as to compression-lock the parts 41, 42, i.e. to prevent the male part 42 from sliding relative to the female part 41 in the opposite direction from the arrow F, even when the screw 56, 57 is loosened.

In this embodiment, the screw 56, 57, when it is tightened (FIG. 9), guarantees the safety of the device by preventing any accidental movement of the female and male parts 41, 42 relative to one another. However, this screw 56, 57 could be eliminated in a variant.

It is clear that with this device, the spacing between the female and male parts 41, 42 can be adjusted simply by distracting these parts until they reach the desired position, without allowing any undesired movement to modify the adjustment before the screw 56, 57 is tightened by compressing the parts 41, 42. This effect is obtained without weakening the male part 42, which does not need to be elastic, and without requiring extremely strict manufacturing tolerances with respect to the external diameter of the male part 42 and the internal diameter of the female part 41.

The invention claimed is:

1. Vertebral replacement device comprising a female part having a longitudinal axis, a male part that is mounted inside the female part and is displaceable axially relative to the female part, and means for axially locking the female and male parts to one another, wherein the locking means comprises:

first and second locking elements mounted so as to be movable in radial translation relative to the female part, in order to occupy a first position at which they cooperate with respective opposing parts of a peripheral surface of the male part to axially lock the female and male parts to one another, and a second position at which the female and male parts are freely displaceable axially relative to one another, and a rotating control element extending radially through the male part, said control element cooperating with the first and second locking elements so that when a rotational movement is communicated to the control element, the control element transforms the rotational movement into a translational movement of each of the locking elements so as to bring the locking elements into either of the first or second positions;

wherein at least the second locking element is rotationally fixed relative to the female part, and the control element is a screw comprising a head and a shaft whose end furthest from the head is threaded and cooperates with a tapping of the second locking element, and in that the first locking element is freely mounted around an unthreaded part of the shaft of the screw near the head, so as to be pushed by the head when the screw is turned in a direction that tends to bring the locking elements into their first position; and wherein the locking elements are subjected to an elastic action that tends to move each of the locking elements away from the male part and to keep the first locking element pressed against the head of the screw.

2. Device according to claim 1, wherein the locking elements are guided in respective housings provided in a peripheral wall of the female part.

3. Device according to claim 1, wherein the locking elements each comprise a notching associated with the female part that cooperates with a complementary notching of a peripheral surface of the male part when the locking elements are in the first position.

4. Device according to claim 1, wherein the first locking element is rotationally fixed relative to the female part.

5. Device according to claim 1, wherein said elastic action is exerted by first and second spring leaves, respectively acting on the first and second locking elements, the spring leaves together being part of a single, unitary part.

6. Device according to claim 1, wherein the control element comprises means for receiving a rotational driving instrument.

7. Device according to claim 1, wherein the male part is hollow and comprises in its peripheral wall first and second opposing oblong holes extending parallel to the longitudinal axis for the passage of the control element.

8. Device according to claim 1, wherein at least one of said parts is attached at its end furthest from the other of said parts to an adjustably inclinable plate, said plate or each of these plates comprising a notched surface having an arc-shaped profile and cooperating with a notched surface of complementary shape of the corresponding part to define the inclination of said plate.

9. Device according to claim 8, wherein the or each adjustably inclinable plate is attached to the corresponding part by means of at least one screw cooperating with a corresponding oblong hole of the plate, said oblong hole being oriented orthogonal to a direction in which the notching of the plate runs.

10. Vertebral replacement device comprising a female part and a male part that is mounted inside the female part and is axially displaceable relative to the female part, a peripheral surface of the male part comprising first formations cooperating with second formations of the device so as to allow a distraction displacement of the female and male parts relative to one another and to compression-lock the female and male parts to one another;

at least one element that is movable in radial translation on the female part, this or these movable element(s) comprising said second formations, and elastic means acting on the movable element or elements so as to maintain the cooperation between the first and second formations;

wherein the elastic means comprises first and second spring leaves, respectively acting on the first and second movable elements, said spring leaves together being part of a single, unitary part.

11. Device according to claim 10, wherein the movable element or elements are guided in one or more corresponding housings provided in a peripheral wall of the female part.

12. Device according to claim 10, wherein the movable element or elements comprise first and second movable elements guided in corresponding diametrically opposed housings provided in a peripheral wall of the female part; and wherein said device further comprises a locking element extending radially through the male part and cooperating with the first and second movable elements, said locking element being arranged to be driven so as to lock the first and second movable elements against the first formations.

13. Device according to claim 12, wherein at least the second movable element is rotationally fixed relative to the female part, the locking element is a screw comprising a head and a shaft whose end furthest from the head is threaded and cooperates with a tapping of the second movable element, and the first movable element is freely mounted around an unthreaded part of the shaft of the screw near the head, so as to be locked by the head against the first formations when the screw is in a tightened position.

* * * * *